United States Patent [19]
Lahti et al.

[11] Patent Number: 4,472,397
[45] Date of Patent: Sep. 18, 1984

[54] USE OF CERTAIN 1-SUBSTITUTED-TRIAZOLO-BENZODIAZEPINES TO TREAT PSYCHOSES

[75] Inventors: Robert Lahti, Galesburg; Robert E. Pyke, Kalamazoo, both of Mich.

[73] Assignee: The Upjohn Company, Kalamazoo, Mich.

[21] Appl. No.: 467,691

[22] Filed: Feb. 18, 1983

[51] Int. Cl.³ .................... A61K 31/41; A61K 31/495
[52] U.S. Cl. .................................... 424/250; 424/269
[58] Field of Search ............................. 424/269, 250

[56] References Cited

U.S. PATENT DOCUMENTS

| | | | |
|---|---|---|---|
| 3,894,025 | 7/1975 | Hester, Jr. | 260/268 TR |
| 4,012,413 | 3/1977 | Hester, Jr. | 260/308 R |
| 4,082,761 | 4/1978 | Hester, Jr. | 260/308 R |
| 4,179,510 | 12/1979 | McCall | 424/267 |
| 4,180,668 | 12/1979 | Hester, Jr. | 260/244.4 |
| 4,250,094 | 2/1981 | Hester, Jr. | 260/245.5 |
| 4,264,615 | 4/1981 | Hester, Jr. | 424/269 |

OTHER PUBLICATIONS

Naunyn-Schmiedeberg's, Achives of Pharmacology, 294, pp. 1-7, (1976), Am. J. Psychiatry, 136, No. 8, Aug., 1979, pp. 1061-1064.
Arch. Gen. Psychiatry, 39, Jul., 1982, pp. 789-794.
The Merck Index, 9th Edition, (1976), p. 310 item 2374—Clozapine.
Two Offline Bibliographies Prepared for Benzodiazepines as Antipsychotics, dated 4/01/82 and 4/02/82 and Retrieved from the Medline Data Base of Bibliographic Retrieval Services, Inc., 1200 Route 7, Latham, New York, 12110.
Amer. J. of Psychiatry, May, 1966, 122 (11), pp. 1292-1293, "Diazepam in . . . Schizophrenia" by N. Borelli et al.
Diseases of the Nervous System, Oct. 1967, 28 (10), pp. 675-678, "A Controlled . . . Schizophrenic Patients" by L. J. Hekimian et al.
The Medical Journal of Australia, 1 (26), Jun. 28, 1969, p. 1387, "Valium . . . Schizophrenia" by B. M. Irvine.
Diseases of the Nervous System, 34 (6), pp. 294-305, (1973), "Patterns . . . Schizophrenia" by E. Laska et al.
The Lancet, Nov. 1, 1975, p. 868, "Are Benzodiazepines Antipsychotic Agents?" by M. Trabucchi.
The Lancet, Nov. 22, 1975, p. 1040, "Are Benzodiazepines Antipsychotic Agents?" by A. Nistri.
Biological Psychiatry, 14, (3), (1979), pp. 557-558, "Benzodiazepines . . . Schizophrenia" by P. Ruskin.
Int. Pharmacopsychiat., 15, pp. 171-179, (1980); "Benzodiazepines . . . Reassessment" by J. N. Nestoros.
Southern Medical Journal, 72, (5), May, 1979, p. 636, "Chlordiazepoxide . . . Agent" by L. H. Lipsuis.
Derwent Abstract No. 52820E/26, Lilly Ind. Ltd., "10-Piperazinyl- . . . Benzodiazepines.
Derwent Abstract No. 19805 E/10; Hoffmann-LaRoche, Inc.-Redn. of Serum Prolactin . . . Benzodiazepine.
Derwent Abstract No. 21463 D/13; Hoffmann-LaRoche Ag-Tranquillisers . . . Nitrazepam.
Am. J. Psychiatry, 139 (4), Apr. 1982; pp. 489-491, "Diazepam in Schizophrenia . . . Trial" by D. C. Jimerson et al.
Acta Psychiat. Scand. 65, (1982), pp. 339-354; "Effect of . . . Estazolam . . . Hallucinations," by O. Lingjaerde.
Schweizer Archiv. fur Neurologi, . . . Band 104, (1969), Issue 1, pp. 102-122, A. Baliarda, "Die Behandlung . . . Valium."
Am. J. Psychiatry, 139, (12), Dec. 1982, pp. 1627-1628, "Clonazepam . . . Schizophrenia".
J. Clinical Psychiatry, 43, (4), Apr. 1982, pp. 160-161, "Diazepam . . . Extrapyramidal Symptoms . . . ".
Neuropsychobiology, 8, pp. 123-128, (1982), "Analgesic . . . Schizophrenia" by S. Haas et al.
American Family Physician, 9 (1), pp. 105-109, (1974), "The Care . . . Patients" by M. Karno.
Int. Pharmacopsychiat. 6, pp. 111-130, (1971), "Das Verhalten . . . Schizophrenen" by V. Mathe et al.
Compr. Psychiatry, 9 (6), pp. 633-643, (1968), "Thioridazine . . . Schizophrenia" by J. M. C. Holden et al.
Med. Welt, Nr. 27, "Anwendung . . . Psychiatrie" by K. Dengler et al.
Deutsches Medizinisches Journal, 20, Nov. 1960, "Langzeitbeobachtungen mit . . . Fachpraxis" by V. W. Durst.

Primary Examiner—Stanley J. Friedman
Attorney, Agent, or Firm—John T. Reynolds

[57] ABSTRACT

Certain 1-(Nitrogen-containing group)-triazolo-benzodiazepines, e.g., adinazolam, are useful for treating psychotic, including schizophrenic, conditions in human patients.

10 Claims, No Drawings

USE OF CERTAIN 1-SUBSTITUTED-TRIAZOLO-BENZODIAZEPINES TO TREAT PSYCHOSES

INTRODUCTION

This invention relates to the use of adinazolam and some other 1-substituted-triazolo-benzodiazepines as antipsychotic drugs, particularly as antischizophrenic drugs.

BACKGROUND OF THE INVENTION

Adinazolam is now an accepted generic name for 8-chloro-1-[(dimethylamino)methyl]-6-phenyl-4H-s-triazolo[4,3-a][1,4]benzodiazepine, and is described and claimed among other compounds in U.S. Pat. No. 4,250,094.

Laboratory studies of chemical compounds as possible antipsychotic drugs have taken the form of observation of effects caused by administration of test compounds in vivo in the $^3$H-Spiroperidol Binding Test which is a standard laboratory animal test for determining whether or not the compound might have activity in combatting psychoses, including schizophrenia in humans in later tests. Compounds defined hereinbelow have shown promising activities in this test.

In humans, studies of the use of candidate drug compounds as antipsychotic drugs have focused on the ability of those drug candidate compounds to control the positive symptoms of schizophrenia such as delusions, hallucinations, positive thought disorder and bizzare behavior. However, it is widely understood that treated schizophrenics remain a problem to themselves and society because of negative symptoms including flattened affect, poverty of expression (alogia), lack of initiative (avolition), anhedonia, attentional impairment and hyposocialization. See "Negative v Positive Schizophrenia" by N. C. Andreason et al. in Arch. Gen. Psychiatry, 39, pp. 789–794 (1982).

Adinazolam and some other 1-amino-triazolo-benzodiazepines have undergone preliminary testing in their in vivo $^3$H-Spiroperidol binding system test in animals, which test is highly selective for antipsychotic active drug compounds. Test results with adinazolam were weak but suggested antipsychotic-like activity. A variety of other compounds of this invention also showed activity in this test.

Antipsychotic activity has been found for the well known benzodiazepine, diazepam. See "Acute High Dose Parenteral Haloperidol Treatment of Psychosis" by Y. Lerner et al. in American J. Psychiatry, 136, pp. 1061–1064 (1979), where the authors report that diazepam was at least as effective as haloperidol over 24 hours of treatment for acute psychosis, but it was also reported that marked sedation effects hampered further consideration of diazepam as an antipsychotic drug of choice.

Those in the art continue to search for antipsychotic drug compounds which will be effective for treating and alleviating the conditions caused by psychoses, including schizophrenia, and at the same time not cause any substantial sedation or hypnotic effects in the patients being treated.

OBJECTS OF THE INVENTION

It is an object of the invention to provide a group of 1-amino-group-triazolo-benzodiazepine compounds which are useful for treating human patients suffering psychoses, or schizophrenic conditions, hopefully with fewer side effects than previously known antipsychotic compounds.

Other objects, advantages and aspects of this invention will become apparent from reading the specification and claims which follow.

SUMMARY OF THE INVENTION

Briefly, we have discovered that adinazolam and certain other 1-amino-group-triazolo-benzodiazepine compounds have been found to be active in the $^3$H-Spiroperidol binding test in animals, indicating their possible usefulness as antipsychotic, including antischizophrenic, drugs. In further preliminary clinical trials with the lead, representative compound, adinazolam, in human patients suffering from forms of intractable psychosis or schizoaffective illnesses, treatment of the patients with small, but effective and safe dosage amounts of adinazolam resulted in improved symptoms of schizophrenia and affective improvement.

DETAILED DESCRIPTION OF THE INVENTION

It has been found according to this invention that an amino-triazolo-benzodiazepine compound having a structural formula

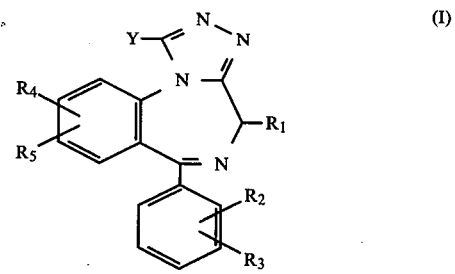

wherein
$R_1$ is hydrogen or $C_1$ to $C_3$-alkyl;
$R_2$, $R_3$, $R_4$ and $R_5$ are hydrogen, $C_1$ to $C_3$-alkyl, fluoro, chloro, bromo, nitro, or trifluoromethyl, and
Y is selected from the group consisting of

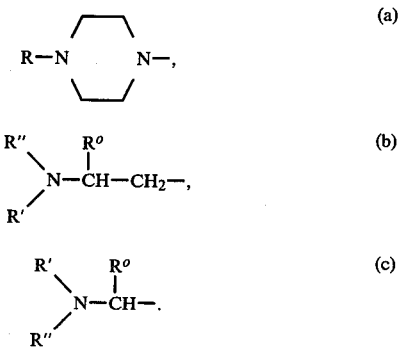

wherein in amino-group (a) above R is hydrogen, $C_1$ to $C_3$-alkyl or B-hydroxyethyl; in amino groups (b) and (c), R' and R" are independently hydrogen or $C_1$ or $C_3$-alkyl, and $R^o$ is hydrogen, or $C_1$ to $C_2$-alkyl, or a pharmacologically acceptable salt thereof, are useful and effective in treating human patients suffering psychoses, including schizophrenic, illnesses.

Examples of compounds of this type include:

adinazolam, 8-chloro-1-[(dimethylamino)methyl]-6-phenyl-4H-s-triazolo[4,3-a][1,4]benzodiazepine and its methanesulfonate salt and other similar compounds described and claimed in Hester, Jr. U.S. Pat. No. 4,250,094.

8-chloro-1-(4-methylpiperazino)-6-phenyl-4H-s-triazolo[4,3-a]-[1,4]benzodiazepine, and other similar compounds described or described and claimed in Hester, Jr. U.S. Pat. No. 3,894,025;

8-chloro-1-[2-(dimethylamino)ethyl]-6-phenyl-4H-s-triazolo[4,3-a][1,4]benzodiazepine, and other similar compounds described or described and claimed in Hester, Jr. U.S. Pat. No. 4,012,413;

and the pharmaceutically acceptable salts thereof.

Pharmaceutically acceptable acid addition salts of the above compounds are prepared by reacting the free base of a compound of Formula (I) with a stoichiometric amount of an acid, such as hydrogen chloride, hydrogen bromide, hydrogen iodide, sulfuric acid, phosphoric acid, acetic acid, propionic acid, butyric acid, lactic acid, citric acid, succinic acid, benzoic acid, methanesulfonic acid, salicyclic acid, pamoic acid, phthalic acid, cyclohexanesulfamic acid, p-toluenesulfonic acid, maleic acid, fumaric acid, and the like.

This invention relates also to pharmaceutical dosage unit forms for systemic administration (oral and parenteral and rectal administration) for treating psychotic and schizophrenic humans. The term "dosage unit form" as used in this specification and in the claims refers to physically discrete units suitable as unitary dosages for mammalian subjects, each unit containing a predetermined quantity of the essential active ingredient, i.e., a compound (I) or a pharmaceutically acceptable acid addition salt thereof, calculated to produce the desired effect, in combination with the required pharmaceutical means which adapt the said ingredient for systemic administration. Examples of dosage unit forms in accordance with this invention are tablets, capsules, orally administered liquid preparations in liquid vehicles, sterile preparations in liquid vehicles for intramuscular and intravenous administration, suppositories, and sterile dry preparations for the extemporaneous preparation of sterile injectable preparations in a liquid vehicle. Solid diluents or carriers for the solid oral pharmaceutical dosage unit forms are selected from the group consisting of lipids, carbohydrates, proteins and mineral solids, for example, starch, sucrose, kaolin, di-calcium phosphate, gelatin, acacia, corn syrup, corn starch, talc and the like. Capsules, both hard and soft, are formulated with conventional diluents and excipients, for example, edible oils, talc, calcium carbonate, calcium stearate and the like. Liquid preparations for oral administration are prepared in water or aqueous or nonaqueous vehicles which advantageously contain suspending agents, such as for example, ethanol, sodium carboxymethylcellulose, acacia, polyvinyl pyrrolidone, polyvinyl alcohol and the like. In the instance of injectable forms, they must be sterile and must be fluid to the extent that easy syringeability exists. Such preparations must be stable under the conditions of manufacture and storage, and ordinarily contain in addition to the basic solvent or suspending liquid, preservatives in the nature of bacteriostatic and fungistatic agents, for example, parabens, chlorobutanol, benzyl alcohol, phenol, thimerosal and the like. In many cases it is preferable to include isotonic agents, for example, isotonic amounts of sugars or sodium chloride. Carriers and vehicles include vegetable oils, ethanol and polyols, for example, glycerol, propylene glycol, liquid polyethylene glycol and the like. Any solid preparations for subsequent extemporaneous preparation of sterile injectable preparations are sterilized, preferably by exposure to a sterilizing gas, such as, for example, ethylene oxide. The aforesaid carriers, vehicles, diluents, excipients, preservatives, isotonic agents and the like constitute the pharmaceutical means which adapt the preparations for systemic administration.

For psychotic, including schizophrenic, disease, a daily dose of 1 to 700 mg is indicated, preferentially 10 to 200 mg; in units of two or three or four subdivided doses, and the exact amount is adjusted based on the weight, age and condition of the patient.

The pharmaceutical dosage unit forms are prepared in accordance with the preceding general description to provide from about 0.5 mg to about 100 mg of the essential active ingredient per dosage unit form. The amount of the essential active ingredient provided in the pharmaceutical dosage unit forms is based on the finding that the effective amount of adinazolam, a representative example of the compounds of the invention and acid addition salts thereof, for obtaining an antipsychotic effect in humans is within a range from about 0.01 mg/kg to about 10 mg/kg, preferably 0.06 to 1.0 mg/kg.

The active ingredients of this invention can also be compounded in combination with other ingredients. The amount of such other active ingredients is to be determined with reference to the usual dosage of each such ingredient. Thus, these active compounds can be combined with hypotensive agents such as $\alpha$-methyldopa (100-250 mg); with diuretics such as hydrochlorothiazide (10-50 mg); tranquilizers such as meprobamate (200-400 mg), diazepam (2-10 mg), muscle relaxants, such as carisoprodol (200-400 mg).

EXAMPLE 1

The following representative compounds were tested in an in vivo mouse $^3$H-Spiroperidol binding test.

| Compound No. | Name |
|---|---|
| 1 | 8-chloro-1-[(dimethylamino)methyl]-6-phenyl-4H—s-triazolo[4,3-a][1,4]-benzodiazepine (adinazolam) |
| 2 | 8-chloro-1-(4-methyl-1-piperazinyl)-6-phenyl-4H—s-triazolo[4,3-a][1,4]benzodiazepine |
| 3 | 8-chloro-1-[2-(dimethylamino)ethyl]-6-phenyl-4H—s-triazolo[4,3-a][1,4]benzodiazepine |
| 4 | 1-(4-methyl-1-piperazinyl)-6-phenyl-4H—s-triazolo[4,3-a][1,4]benzodiazepine |
| 5 | 8-chloro-1-(4-methyl-1-piperazinyl)-4-methyl-5,6-dihydro-6-phenyl-4H—s-triazolo[4,3-a][1,4]benzodiazepine |
| 6 | 1-(4-methyl-1-piperazinyl)-6-(2-chlorophenyl)-4H—s-triazolo[4,3-a][1,4]benzodiazepine |
| 7 | 1-(4-ethyl-1-piperazinyl)-6-(2-chlorophenyl)-4H—s-triazolo[4,3][1,4]benzodiazepine |
| Control/Standard | Clozapine |

The test procedure was as follows:

Male ICR mice weighing 20–22 g were used. The mice were pretreated with test drug solutions or vehicle mixtures subcutaneously one hour before injection of 66 micro Curie/kg, in 0.2 ml, of $^3$H-Spiroperidol (specific activity of 29.9 Curie per mmole). The test drug compounds were dissolved in saline, 1M citric acid in water or 33% propylene glycol in water solution, and then diluted to volume with saline.

The animals were dosed with the $^3$H-Spiroperidol solution at 66 micro-Curie/kg in 0.2 ml, by the subcutaneous route. The animals were sacrificed 2 hours later and sections of the brains of the mice were removed with striata and septum and some adjacent cortex. The tissues were weighed after freezing on dry ice and dissolved in 1 ml of Protosol overnight at 35° C. The Protosol was neutralized with 80 μl of 6N hydrochloric acid and 15 ml of ACS scintillation fluid was added. All samples were then counted in a liquid scintillation counter.

A background of 25 counts per minute (CPM) was subtracted from the counts for each sample counted. The CPM/mg of the tissue was calculated and a statistical t test was used to test the significance of the value.

In this test the in vivo $^3$H-spiroperidol binding assay test values for the above compounds 1 to 7 were as follows:

| Compound | Dose (mg/kg) | In vivo $^3$H—Spiroperidol % of Control |
|---|---|---|
| 1 | 50 | 82% |
| 2 | 50 | 69% |
|   |    | 73% |
| 3 | 50 | 78% |
| 4 | 50 | 59% |
| 5 | 50 | 89% |
| 6 | 50 | 65% |
| 7 | 50 | 72% |
| Standard Drug Clozapine | 15 | 65% |

These data indicate these compounds are all active. Since the above drugs are inhibitors of the binding of $^3$H-Spiroperidol (an antipsychotic agent), it was concluded that they might well be active as antipsychotic, including antischizophrenic, drugs.

EXAMPLE 2

In a human patient, adinazolam was given for two days at a dosage of 5 mg bid (twice a day) the first day and 5 mg tid (three times a day) the second day to a human schizoaffective patient suffering moodcongruent delusions and persecutory auditory hallucinations which had been refractory to four months of therapy with a tricyclic antidepressant and stelazine. The clinician serving the patient found a remarkable approximately fifty percent (50%) improvement in the patient's condition over the two days of treatment with adinazolam.

EXAMPLE 3

Clinical trials with the lead compound, adinazolam, in the treatment of human patients for psychotic, including schizophrenic, disorders in the absence of depression are in progress. Five patients have been treated and all experienced moderate or marked improvement. Patients are being maintained on dosages of from 2.5 to 20 mg. of adinazolam qid (four times a day). One patient showed a dramatic effect when medication was unintentionally withdrawn for 24 hours. The patient reverted to a psychotic condition during this 24 hour period. Following this period, when adinazolam therapy was reinitiated in the morning the patient became lucid again that same day.

It is hoped that the trials will show that adinazolam possesses important safety advantages over known standard antipsychotic drugs: lack of extrapyramidal side effects, lack of sedation effect, lack of tardive diskinesia, and lack of serum prolactin elevation. In one patient extrapyramidal side effects persisting from previous medication disappeared with adinazolam therapy.

Elevations in striatal homovanillic acid (HVA) may be taken as an indicator of the propensity of an antipsychotic drug to induce extrapyramidal side effects and tardive dyskinesia. Benzodiazepines reverse this HVA elevating effect, Arch. Pharmacol., 294, pp. 1–7, "Interaction of Benzodiazepines with Neuroleptics at Central Dopamine Neurons" by H. H. Keller et al. Thus, benzodiazepines may also reverse extra pyramidal side effects and tardive dyskinesia as well. Neuroendocrine effects of antipsychotic drugs are a very predominant side effect, especially prolactin elevations. The finding that benzodiazepines can reverse the prolactin elevating effect in rats ("Anterior Pituitary GABA Receptors and Their Regulation of Prolactin Secretion, GABA and Benzodiazepine Receptors" by L. Grandison, edited by E. Costa et al., Raven Press, New York 1981) is firm support for the above observed effect on HVA.

Consistent with the above scientific literature, adinazolam had no apparent elevating effect on serum prolactin levels in the open-label depression studies. In four human patients (2 males; 2 females) with elevated prolactin levels at the introductory screening physicals, the prolactin levels in all four patients normalized during treatment with adinazolam. (Three of the patients had been treated recently with a phenothiazine or amoxapine).

We claim:

1. A method of treating psychoses in a human which comprises administering to such psychotic human an antipsychotic dose of an amino-triazolo-benzodiazepine compound having the formula

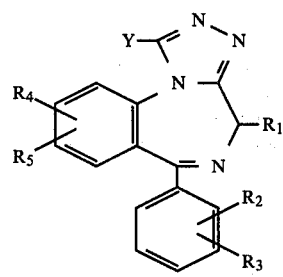

(I)

wherein $R_1$ is hydrogen or $C_1$ to $C_3$-alkyl;

$R_2$, $R_3$, $R_4$ and $R_5$ are hydrogen, $C_1$ to $C_3$-alkyl, fluoro, chloro, bromo, nitro, or trifluoromethyl; and Y is selected from the group consisting of

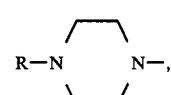

(a)

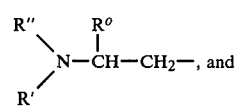

(b)

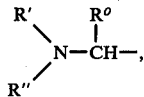 (c)

wherein in the amino group (a) above, R is hydrogen, $C_1$ to $C_3$-alkyl or $\beta$-hydroxyethyl, and in the amino groups (b) and (c) above, R' and R" are independently hydrogen or $C_1$ to $C_3$-alkyl, and $R^o$ is hydrogen or $C_1$ to $C_2$-alkyl, or a pharmacologically acceptable salt thereof.

2. A method according to claim 1 wherein the amino-triazolobenzodiazepine compound is a compound wherein Y is

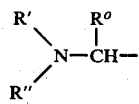

wherein $R^o$ is hydrogen or $C_1$ to $C_2$-alkyl;
R' and R" are each $C_1$ to $C_3$-alkyl,
or a pharmacologically acceptable salt thereof.

3. A method according to claim 2 wherein the compound is 8-chloro-1-[(dimethylamino)methyl]-6-phenyl-4H-s-triazolo[4,3-a][1,4]benzodiazepine, or a pharmacologically acceptable salt thereof.

4. A method according to claim 3 wherein the compound is 8-chloro-1-[(dimethylamino)methyl]-6-phenyl-4H-s-triazolo[1,4-a][1,4]benzodiazepine methanesulfonate.

5. A method according to claim 1 wherein the amino-triazolobenzodiazepine compound is a compound wherein Y is

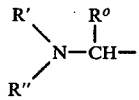

wherein $R^o$ is hydrogen or $C_1$ to $C_2$-alkyl;
R' and R" are each hydrogen or $C_1$ to $C_3$-alkyl.

6. A method according to claim 1 wherein the amino-triazolobenzodiazepine compound is a compound wherein Y is

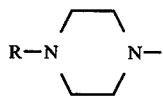

wherein R is hydrogen, $C_1$–$C_3$-alkyl or $\beta$-hydroxyethyl.

7. A method according to claim 1 wherein the amino-triazolobenzodiazepine compound is a compound wherein Y is

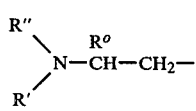

wherein R' and R" are independently hydrogen or $C_1$ to $C_3$-alkyl and $R^o$ is hydrogen or $C_1$ to $C_2$-alkyl.

8. A method in accordance with claim 1 of treating schizophrenia in a human which comprises administering to such schizophrenic human an antischizophrenic dose of an amino-triazolo-benzodiazepine compound having the formula

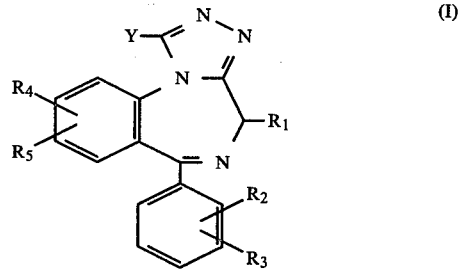 (I)

wherein $R_1$ is hydrogen or $C_1$ to $C_3$-alkyl;
$R_2$, $R_3$, $R_4$ and $R_5$ are hydrogen, $C_1$ to $C_3$-alkyl, fluoro, chloro, bromo, nitro, or trifluoromethyl; and
Y is selected from the group consisting of

 (a)

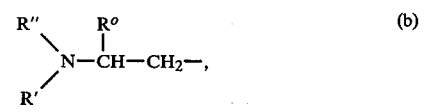 (b)

and

 (c)

wherein in the amino group (a) above, R is hydrogen, $C_1$ to $C_3$-alkyl or $\beta$-hydroxyethyl, and in the amino group (b) and (c) above, R' and R" are independently hydrogen or $C_1$ to $C^3$-alkyl, and $R^o$ is hydrogen or $C_1$ to $C_2$-alkyl, or a pharmacologically acceptable salt thereof.

9. A method according to claim 8 wherein the amino-triazolobenzodiazepine compound is a compound wherein Y is

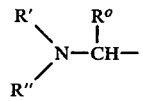

wherein $R^o$ is hydrogen or $C_1$ to $C_2$-alkyl;
R' and R" are each $C_1$ to $C_3$-alkyl,
or a pharmacologically acceptable salt thereof.

10. A method according to claim 9 wherein the compound is 8-chloro-1-[(dimethylamino)methyl]-6-phenyl-4H-s-triazolo[4,3a][1,4]benzodiazepine, or a pharmacologically acceptable salt thereof.

* * * * *

UNITED STATES PATENT OFFICE
CERTIFICATE OF CORRECTION

Patent No. 4,472,397  Dated September 18, 1984

Inventor(s) Robert Lahti et al

It is certified that error appears in the above-identified patent and that said Letters Patent are hereby corrected as shown below:

Column 7, line 32, "triazolo[1,4-a][1,4]benzo ..." should read -- triazolo[4,3-a][1,4]benzo ... --.

Signed and Sealed this

Twenty-first Day of May 1985

[SEAL]

Attest:

DONALD J. QUIGG

Attesting Officer  Acting Commissioner of Patents and Trademarks